(12) United States Patent
Cavassini et al.

(10) Patent No.: US 8,679,546 B2
(45) Date of Patent: *Mar. 25, 2014

(54) RUMINANT FEED PELLET COMPOSITION WITH CONTROLLED RELEASE OF PHYSIOLOGICALLY ACTIVE SUBSTANCES, AND PROCEDURE FOR PREPARATION AND USE THEREOF

(75) Inventors: Paolo Cavassini, Ravenna (IT); Paolo Cicognani, Predappio (IT); Jean Antoine Meiners, Cormondreche (CH)

(73) Assignee: Valentini S.R.L., Bertinoro (IT)

( * ) Notice: Subject to any disclaimer, the term of this patent is extended or adjusted under 35 U.S.C. 154(b) by 1450 days.

This patent is subject to a terminal disclaimer.

(21) Appl. No.: 11/228,818

(22) Filed: Sep. 16, 2005

(65) Prior Publication Data

US 2006/0067984 A1    Mar. 30, 2006

(30) Foreign Application Priority Data

Sep. 24, 2004  (IT) .............................. MI2004A1820

(51) Int. Cl.
*A61K 9/14*    (2006.01)
*A61K 31/14*   (2006.01)

(52) U.S. Cl.
USPC ............ 424/498; 424/489; 424/502; 514/642

(58) Field of Classification Search
None
See application file for complete search history.

(56) References Cited

U.S. PATENT DOCUMENTS

| | | | |
|---|---|---|---|
| 4,394,377 A | 7/1983 | Spires | |
| 4,832,967 A * | 5/1989 | Autant et al. | 426/96 |
| 4,948,589 A | 8/1990 | Iijima et al. | |
| 5,190,775 A | 3/1993 | Klose | |
| 5,429,832 A * | 7/1995 | Ueda et al. | 426/96 |
| 5,496,571 A | 3/1996 | Blagdon et al. | |
| 5,571,527 A | 11/1996 | Nishimura et al. | |
| 5,766,668 A | 6/1998 | Brommelsiek et al. | |
| 6,106,871 A | 8/2000 | Miller | |
| 6,174,890 B1 | 1/2001 | Riga et al. | |
| 6,299,912 B1 | 10/2001 | Ito et al. | |
| 6,797,291 B2 | 9/2004 | Richardson | |
| 2003/0129295 A1 * | 7/2003 | Richardson | 426/635 |
| 2003/0148013 A1 * | 8/2003 | Jobe et al. | 426/635 |
| 2005/0019413 A1 * | 1/2005 | Cavassini et al. | 424/489 |
| 2006/0067984 A1 | 3/2006 | Cavassini | |

FOREIGN PATENT DOCUMENTS

| | | | | |
|---|---|---|---|---|
| CA | 2256256 A1 | 6/2000 | | |
| EP | 0619079 A2 | 10/1994 | | |
| WO | 02082921 A1 | 10/2002 | | |
| WO | WO 03/033031 | * | 4/2003 | ............... A61K 9/52 |

OTHER PUBLICATIONS

Melting Point of hydrogenated soybean oil. Accessed Jul. 22, 2008 via http://www.parchem.com/Soybean-Oil,-hydrogenated-NF-001363.aspx.*

* cited by examiner

*Primary Examiner* — Kevin S Orwig
(74) *Attorney, Agent, or Firm* — Pearne & Gordon LLP

(57) ABSTRACT

The subject of this invention is a controlled release composition for zootechnical use. In particular, the subject of this invention is a composition comprising micro-pellets that are able to release the physiologically active substances they contain in a controlled manner. In addition, this invention refers to a procedure for preparing said composition as well as the use of said composition in the zootechnical sector.

23 Claims, 2 Drawing Sheets

RUMINANT FEED PELLET COMPOSITION WITH CONTROLLED RELEASE OF PHYSIOLOGICALLY ACTIVE SUBSTANCES, AND PROCEDURE FOR PREPARATION AND USE THEREOF

TECHNICAL FIELD OF THE INVENTION

The subject of this invention is a controlled release composition for zootechnical use. In particular, the subject of this invention is a composition comprising micro-pellets that are able to release the physiologically active substances they contain in a controlled manner. In addition, this invention refers to a procedure for preparing said composition as well as the use of said composition in the zootechnical sector.

BACKGROUND OF THE INVENTION

It is known to use physiologically active substances (hereinafter active substances) to supplement or add additives to the diet of farm animals in order to improve their conditions of health and their productive performance.

Active substances of interest include amino acids, vitamins, enzymes, nutrients such as proteins and carbohydrates, probiotic micro-organisms, prebiotic foods, mineral salts, choline and its derivatives.

Some of the above-mentioned substances are already normally present in foods used for feeding animals. However, sometimes the addition of said active substances, present in the diet, may be insufficient or inadequate to cope with states of deficiency or situations of high productivity.

These active substances, with nutritional properties, are administered to the animals orally via the preparation of formula products (premixes or complementary feeds) in which said active substances are "diluted" by mechanical mixing with a medium; the ensuing product is ready to be added to the final food (feed).

The active substances and the feed containing said active substances suffer chemical-enzymatic degradation, before reaching the intestine, in the first section of the animal's digestive tract. In the case of ruminants (that have four digestive compartments) the degradation can be particularly intense because of two main concomitant factors: a lengthy transit time of the food in the prestomachs (particularly in the rumen) and the presence of microbial flora that performs an action of degradation on most of the molecules passing through the rumen.

The microbial action of the ruminal micro-organisms chemically alters some active substances, such as choline for instance, transforming them into substances with a lower value of nourishment or with significantly less biological activity than in the initial compound.

In addition, the formula products containing the above-mentioned active substances suffer degradation during their preparation, especially in the phases of mixing, packing and storage, as well as in their technological treatments such as agglomeration (dicing or pelletizing) by applying heat and/or vapour pressure.

To reduce the above-mentioned drawbacks, it has been proposed to encapsulate or coat some active substances biologically for zootechnical use with a film of pH sensitive material resistant to the gastric environment by using polymers such as: polyvinylpyrrolidone, polyamides and celluloses that have been chemically modified.

This solution has the drawback of a high production cost, combined with the fact that using synthetic polymers introduces non-physiological substances into the animals' diet.

Another solution put forward is to protect the biologically active substances for zootechnical use with controlled release in the intestine of the animals with some substances of vegetable origin.

This solution does not guarantee satisfactory protection of the biologically active substances from attacks made by microbial flora or digestive enzymes before reaching the intestine.

Some formulations are known on the market that contain the biologically active substances in a rumen-protected form (that is protected from degradation by the ruminal ecosystem).

A rumen-protected formulation has the capacity to pass through the rumen, without being substantially decomposed, and to carry the protected substance, at a later point to the rumen, allowing release of the active substance.

Therefore, for an efficient contribution of biologically active substances to ruminants, a rumen-protected formulation or ruminal bypass must be able to permit crossing the rumen and releasing the protected active substance in the abomasum and/or in the digestive tract following it.

Therefore it remains necessary to be able to have a composition for zootechnical use that is able to release the substances it physiologically contains in a controlled manner, which does not have the drawbacks of the compositions available on the market.

In addition, there remains the need to be able to have a composition with controlled release of physiologically active substances that have particular mechanical-structural characteristics such as resistance to mixing also with mineral media and resistance to thermal stresses (pelletizing or dicing).

SUMMARY OF THE INVENTION

An initial purpose is to provide a composition for zootechnical use that releases the physiologically active substances it contains in a controlled manner in order to reduce the degradation caused by the bacterial flora and by the production of endogenous enzymes.

Another purpose is to provide a composition for zootechnical use with controlled release having chemical and physical properties such as to allow the preparation of formula products resistant to mechanical-structural degradation.

These purposes and others that will be clear from the following detailed description have been reached by the Applicant who has perfected a procedure for preparing micro-pellets capable of releasing the active substances they contain in a controlled manner, composed of a core and an external coating of two layers.

The micro-pellets, in the case of ruminants, permit localized controlled release of the active substances primarily carried into the post-ruminal zone, from the abomasum to the small intestine, and their following absorption in a non-degraded form.

The first subject of this invention is a composition for zootechnical use with controlled release having the characteristics stated in the attached independent claim.

Another subject of this invention is a procedure to prepare a composition for zootechnical use with controlled release having the characteristics stated in the attached independent claim.

Yet another subject of this invention is the use of a composition for zootechnical use with controlled release having the characteristics stated in the attached independent claim.

The invention is illustrated in greater detail in the description that follows with the aid of some forms of embodiment, given merely by way of example and, therefore, not restrictive.

DESCRIPTION OF THE INVENTION

Figure 1:
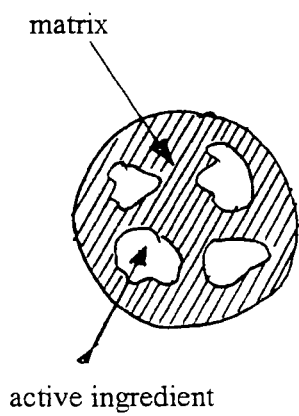
FIG. 1 shows the cross-section of a micro-pellet according to the present invention.

The composition subject of this invention comprises micro-pellets composed of a core and a coating outside this core.

The core comprises a physiologically active substance or active ingredient (hereinafter, for brevity, active substance) and a matrix.

The matrix comprises excipients selected from binding substances, inert ingredients and flow-control substances that together aid the formation of the pellets.

The external coating comprises an initial layer composed of a substance that forms a water-repellent film that is stable under the conditions in the rumen for at least 8 hours and a second impact-resistant layer that withstands temperatures of between 80 and 100° C.

The core comprises one or more active substances, generally in a solid form, and must be firm enough so as to remain intact during the following phases of processing, especially during the operations of coating.

Within the context of this invention the term physiologically active substance is used to mean: amino acids, vitamins, enzymes, nutrients such as proteins and carbohydrates, probiotic micro-organisms, prebiotic foods, mineral salts, mixes of acids such as for instance lactic acid, fumaric acid, citric acid and malic acid, choline and choline derivatives such as for instance choline chloride, choline bi-tartrate, dehydrogenated citrate of choline, choline bicarbonate, choline sulphate and choline hydroxide.

These active substances can be used on their own or mixed together in varying weight ratios.

In one preferred embodiment the active substance is selected from: methionine, choline, choline chloride, lysine, vitamin C, vitamin C acetate, vitamin E, vitamin B2, vitamin PP and a mixture of acids comprising lactic acid, fumaric, citric and malic acid.

The preparation procedure includes a phase in which the active substance is mixed with one or more substances with a binding action (hereinafter, for brevity, binder) and with inert ingredients to obtain a uniform heterogeneous mixture.

The mixing is done in a container equipped with mixing, cutting and heating equipment.

The mixture obtained is hot extruded so as to obtain micro-pellets of the required shape and dimensions. The pellets must be strong enough to withstand impact against the walls of the fluid bed during the phases of coating. In addition, the pellets must withstand crushing in order to withstand the pressure exerted during the pelletizing process to which the feed in which the pellets are added may be subjected.

The parameter used to evaluate the impact resistance of a micro-pellet is the impact resistance generated on dropping the particle onto a metal plate. The minimum height that the particle must withstand is 3 meters.

It has been evaluated that the crushing resistance must be greater than a pressure of 0.575 $N/mm^2$.

The extrusion is made in an extruder that is known to sector experts. The extruder is equipped with a feeding and mixing chamber, a plurality of sectors equipped with heating so as to have a temperature gradient according to the processing. The mixing and extrusion proper are achieved by one or more screw conveyors depending on the type of extruder.

The head of the extruder is equipped with a die plate equipped with heating. The die plate contains a plurality of outlet holes with a preset diameter. Clearly, if it is wished to change format the die plate can be replaced.

The extruded composition leaves the head of the die plate at a temperature of from 40 to 80° C. and in a shape that is, for instance, cylindrical, triangular or rhomboid.

At the outlet from the die plate the composition is subjected to cutting by a cutter at variable speed that permits adjusting the length of the micro-pellets.

The binders, used in the formation of the matrix, are composed of non-toxic substances of vegetable or synthetic origin such as rubbers, cellulose and its derivatives, starches and derivatives, waxes and derivatives and fats and derivatives.

Advantageously, vegetable waxes such as carnauba wax and microcrystalline waxes are used.

In a preferred embodiment, the binder is a combination of carnauba wax and microcrystalline wax in a weight ratio from 1:3 to 3:1; advantageously 1:1. Alternatively, the binder is a microcrystalline wax.

The choice of binders is very important as they give the matrix the necessary chemical and physical properties that, combined with the properties given by the coating, make it possible to obtain ruminal bypass micro-pellets.

The inert ingredients, used in the formation of the matrix, are free flowing substances and they generally belong to the category of silicates, especially hydrophobic silicates such as for instance colloidal silica, amorphous synthetic silica, precipitated silica, sodium aluminium silicates, calcium silicate, talc, kaolin, synthetic hydrophobic zeolites.

Sometimes there is an antioxidant for fatty substances such as BHT (Butyl-Hydroxy-Toluene).

The matrix enveloping the active ingredient (see FIG. 1) performs not only a purely mechanical function but also that of delaying the release of the active ingredient in the rumen.

After forming pellets of a suitable size they go through a coating phase to give them a coating.

The coating comprises a first and a second layer.

The first layer is formed of a physiologically acceptable substance with hydrophobic properties that is ruminal-stable for at least 8 hours.

These hydrophobic substances that form said first layer are selected from the group consisting of: fats, fatty acids, hydrogenated oils, mono- and di-glycerides of fatty acids, esters of fatty acids and fatty alcohols, with chains containing from 12 to 22 atoms of carbon and a melting point of from 40 to 74° C.

These hydrophobic substances are selected from: lauric acid, stearic acid, palmitic acid, stearine, hydrogenated soya oil, hydrogenated cotton oil, hydrogenated palm oil, hydrogenated linseed oil, sodium glyceril mono-, di-, tri-stearate, calcium stearate (Tmelt. 147-149° C.), magnesium stearate (Tmelt. 147-149° C.), stearyl alcohol, cetyl stearyl alcohol.

The aforesaid hydrophobic substances are selected from those mentioned above with a melting point of from 60 to 64° C.

Advantageously the hydrophobic substances are selected from hydrogenated palm oil and/or hydrogenated soya oil.

|  | Unit of measurement | Limits |
| --- | --- | --- |
| Hydrogenated palm oil | | |
| Moisture | % | 0.2 max |
| Melting range | ° C. | 60-64 |
| Acidity no. | mg KOH/g | 8 max |
| No. of peroxides | Meq.O$_2$/kg | 1 max |
| Iodine no. (Wijs) | gI/100 g | 1-4 |
| Saponification no. | mg KOH/g | 195-205 |
| Not saponifiable | % | 0.8 max |
| Hydrogenated soya oil | | |
| Moisture | % | 0.2 max |
| Melting range | ° C. | 60-64 |
| Acidity no. | mg KOH/g | 6 max |
| No. of peroxides | Meq.O$_2$/kg | 1 max |
| Iodine no. (Wijs) | gI/100 g | 0.2-1 |
| Saponification no. | mg KOH/g | 190-200 |
| Free fatty acids | % | 0.1 max |

The second layer comprises a second physiologically acceptable substance (or a mixture of substances) with hydrophobic properties (second hydrophobic substance) that is resistant to mechanical stress and keeps its chemical-physical properties unchanged up to a temperature of 80° C.

Said second hydrophobic substance that forms said second layer is selected from the group consisting of microcrystalline waxes, paraffin waxes, vegetable waxes and synthetic waxes with a melting point of from 80 to 100° C. Advantageously said second hydrophobic substance is selected from carnauba wax and/or microcrystalline waxes.

Waxes derived from petroleum are natural waxes and are divided into three types: paraffin waxes, semi-crystalline waxes and microcrystalline waxes.

Paraffin wax is derived from petroleum consisting mainly of alkanes.

Microcrystalline wax is derived from petroleum containing branched and cyclic saturated hydrocarbons in varying proportions in addition to the alkanes.

Semi-crystalline wax contains more cyclic and branched compounds than paraffin wax, but less than microcrystalline wax.

A system of classification is based on the index of refraction of the wax and on its freezing point as determined by ASTM D938.

| Waxes derived from petroleum | | |
| --- | --- | --- |
| | Wax | |
| Property | Paraffin | Microcrystalline |
| Flash point | 204° C. | 260° C. |
| Viscosity in centipoise | 4.2-7.4 | 10.2-25 |
| Freezing point | 46-68° C. | 60-93° C. |
| Index of refraction | 1.430-1.433 | 1.435-1.445 |
| Average molecular weight | 350-420 | 600-800 |
| Atoms of carbon per molecule | 20-36 | 30-75 |

According to USP 26-NF 21 microcrystalline waxes have melting points that can vary from 54 to 102° C.

The micro-pellets subject of this invention have a substantially cylindrical shape with a diameter of from 0.5 to 5 mm; preferably from 0.8 to 1.2 mm and a length of from 0.5 to 5 mm; preferably from 0.8 to 2.0 mm.

The micro-pellets can be prepared by means of common techniques of extrusion and preferably with a thermostatted twin-screw extruder, with sectors, with the possibility of checking and varying the temperature in the different sectors so as to be able to use different types of binding agents and allow the binder to penetrate the active substance and the excipients so as to form a pellet with the required mechanical-structural characteristics.

The surface treatment of the core, to form the first and second layer, is performed in a fluid bed with the technique of "hot melt coating."

By way of example, there follows a non-restrictive example of the preparation of a coating in a 5 kg pilot system.

Introduce 2.5 kg of micropellets obtained by extrusion into the container. Hermetically close the container and add air flow at a rate of 6000/6500 m$^3$/hour, to take the temperature of the air and product to 40° C. When the temperature of the product has reached the established value begin spraying the hydrogenated soya oil (HSO) maintained at a temperature of 105° C. taking care to maintain the temperature of the product at 40° C. Spray 1.2 kg of HSO at a speed of 30 g/min. At the end of this first phase the first coating is formed.

Immediately after the end of spraying the HSO, the carnauba wax is begun to be sprayed, maintained at a temperature of 115° C., again keeping the temperature of the product at 40° C. Spray 800 g of carnauba at a speed of 20 g/min. At the end of this second phase the second coating is formed.

DESCRIPTION OF THE PREFERRED EMBODIMENTS

This invention is described with the aid of some examples of embodiment that have a merely illustrative purpose and are not restrictive.

Example 1

Dl-Methionine 820 g of dl-methionine powder with an average diameter of from 0.4 to 0.7 mm is mixed with 60 g of carnauba wax, 60 g of microcrystalline wax, 54 g of colloidal silica and 6 g of magnesium stearate. The mixture is then made to pass through the extruder setting the temperatures of the different sectors with the following programme:

| Sector 1 | Sector 2 | Sector 3 | Sector 4 | Sector 5 | die |
| --- | --- | --- | --- | --- | --- |
| 70° C. | 90° C. | 55° C. | 50° C. | 40° C. | 65° C. |

The granules obtained in the form of cylindrical micro-pellets have a concentration of dl-methionine equal to 80% and are coated in a fluid bed with a first layer composed of hydrogenated palm oil (first hydrophobic substance) and a second layer composed of carnauba wax (second hydrophobic substance), for a total weight of 140 g (ratio between the two layers 6:4), to obtain a finished product containing 70% of dl-methionine compared to the total weight of the composition. The results of the release in vitro are given in chart 1.

Example 2

Choline Chloride 819 g of choline chloride in crystals with an average diameter that can vary from 0.5 to 1.0 mm is mixed with 60 g of carnauba wax, 60 g of microcrystalline wax, 55 g of colloidal silica and 6 g of magnesium stearate. The mixture is then made to pass through the extruder setting the temperatures of the different sectors with the following programme:

| Sector 1 | Sector 2 | Sector 3 | Sector 4 | Sector 5 | die |
|---|---|---|---|---|---|
| 65° C. | 85° C. | 55° C. | 45° C. | 40° C. | 65° C. |

The granules obtained in the form of cylindrical micropellets have a concentration of choline chloride equal to 80% and are coated in a fluid bed with a first layer composed of hydrogenated palm oil and a second layer composed of carnauba wax, for a total weight of 140 g (ratio between the two layers 6:4), to obtain a finished product containing 70% of choline chloride compared to the total weight of the composition. The results of the release in vitro are given in chart 1.

CHART 7

| | | % release at 37° C. pH 5.8 | | | |
|---|---|---|---|---|---|
| Example | Titre % | After 1 hour | After 2 hours | After 5 hours | After 8 hours |
| 1 | 70.2 | 2 | 3.5 | 6 | 10 |
| 2 | 70.4 | 62 | 100 | / | / |

These examples tell us that it is much more difficult to protect the highly water-soluble choline chloride than the poorly water-soluble methionine.

Example 3

Choline Chloride 819 g of choline chloride in crystals with an average diameter of from 0.5 to 1.0 mm is mixed with 60 g of carnauba wax, 60 g of microcrystalline wax, 55 g of colloidal silica and 6 g of magnesium stearate. The mixture is then made to pass through the extruder setting the temperatures of the different sectors with the following programme:

| Sector 1 | Sector 2 | Sector 3 | Sector 4 | Sector 5 | die |
|---|---|---|---|---|---|
| 65° C. | 85° C. | 55° C. | 45° C. | 40° C. | 65° C. |

The granules obtained in the form of cylindrical micropellets have a concentration of choline chloride equal to 80% and are coated in a fluid bed with a first layer composed of hydrogenated palm oil and a second layer composed of carnauba wax, for a total weight of 1,000 g (ratio between the two layers 6:4), to obtain a finished product containing 40% of choline chloride. The results of the release in vitro are given in chart 2.

Example 4

Choline Chloride 819 g of choline chloride in crystals with an average diameter of from 0.5 to 1.0 mm is mixed with 60 g of carnauba wax, 60 g of microcrystalline wax, 55 g of colloidal silica and 6 g of magnesium stearate. The mixture is then made to pass through the extruder setting the temperatures of the different sectors with the following programme:

| Sector 1 | Sector 2 | Sector 3 | Sector 4 | Sector 5 | die |
|---|---|---|---|---|---|
| 65° C. | 85° C. | 55° C. | 45° C. | 40° C. | 65° C. |

The granules obtained in the form of cylindrical micropellets have a concentration of choline chloride equal to 80% and are coated in a fluid bed with a first layer composed of hydrogenated soya oil and a second layer composed of carnauba wax, for a total weight of 600 g (ratio between the two layers 6:4), to obtain a finished product containing 50% of choline chloride. The results of the release in vitro are given in chart 2.

CHART 2

| | | % release at 37° C. pH 5.8 | | | |
|---|---|---|---|---|---|
| Example | Titre % | After 1 hour | After 2 hours | After 5 hours | After 8 hours |
| 3 | 40.7 | 0 | 1.2 | 2 | 4.8 |
| 4 | 50.1 | 0.3 | 2.3 | 3.8 | 8.6 |

Example 5

L-Lysine 810 g of l-lysine granular powder with an average diameter of from 0.2 to 1.2 mm is mixed with 92 g of carnauba wax, 92 g of microcrystalline wax and 6 g of magnesium stearate. The mixture is then made to pass through the extruder setting the temperatures of the different sectors with the following programme:

| Sector 1 | Sector 2 | Sector 3 | Sector 4 | Sector 5 | die |
|---|---|---|---|---|---|
| 65° C. | 85° C. | 50° C. | 45° C. | 40° C. | 70° C. |

The granules obtained have a concentration of l-lysine HCl equal to 80% and are coated in a fluid bed with a first layer composed of hydrogenated soya oil and a second layer composed of carnauba wax, for a total weight of 140 g (ratio between the two layers 6:4), to obtain a finished product containing 70% of l-lysine HCl. The results of the release in vitro are given in chart 3.

Example 6

L-Lysine HCl 860 g of l-lysine HCl granular powder with an average diameter of from 0.2 to 1.2 mm is mixed with 134 g of microcrystalline wax and 6 g of magnesium stearate, the mixture is then made to pass through the extruder setting the temperatures of the different sectors with the following programme:

| Sector 1 | Sector 2 | Sector 3 | Sector 4 | Sector 5 | Die |
|---|---|---|---|---|---|
| 65° C. | 80° C. | 55° C. | 45° C. | 45° C. | 65° C. |

The granules obtained have a concentration of l-lysine HCl equal to 85% and are coated in a fluid bed with a first layer composed of hydrogenated soya oil and a second layer composed of carnauba wax, for a total weight of 400 g (ratio between the two layers 6:4), to obtain a finished product containing 60% of l-lysine HCl. The results of the release in vitro are given in chart 3.

Example 7

L-Lysine 810 g of l-lysine HCl granular powder with an average diameter of from 0.2 to 1.2 mm is mixed with 184 g of microcrystalline wax and 6 g of magnesium stearate. The mixture is then made to pass through the extruder setting the temperatures of the different sectors with the following programme:

| Sector 1 | Sector 2 | Sector 3 | Sector 4 | Sector 5 | Die |
|---|---|---|---|---|---|
| 70° C. | 90° C. | 60° C. | 45° C. | 45° C. | 65° C. |

The granules obtained in the form of cylindrical micropellets have a concentration of l-lysine HCl equal to 80% and are coated in a fluid bed with a first layer composed of hydrogenated soya oil and a second layer composed of carnauba wax, for a total weight of 600 g (ratio between the two layers 6:4), to obtain a finished product containing 50% of l-lysine HCl. The results of the release in vitro are given in chart 3.

CHART 3

| | | % release at 37° C. pH 5.8 | | | |
|---|---|---|---|---|---|
| Example | Titre % (Lysine HCl) | After 1 hour | After 2 hours | After 5 hours | After 8 hours |
| 5 | 70.0 | 9.5 | 15.7 | 33.6 | 60.2 |
| 6 | 60.2 | 2.2 | 9.1 | 22.4 | 31.1 |
| 7 | 51.2 | 0.8 | 1.4 | 4.6 | 10.3 |

These examples tell us that it is extremely difficult to protect the highly water-soluble lysine HCl too.

Example 8

Vitamin C 816 g of vitamin C crystals with an average diameter of 0.5 mm are mixed with 92 g of carnauba wax, 90 g of microcrystalline wax, 2 g of BHT and 6 g of magnesium stearate, the mixture is then made to pass through the extruder setting the temperatures of the different sectors with the following programme:

| Sector 1 | Sector 2 | Sector 3 | Sector 4 | Sector 5 | die |
|---|---|---|---|---|---|
| 60° C. | 75° C. | 50° C. | 45° C. | 40° C. | 65° C. |

The granules obtained have a concentration of vitamin C equal to 80% and are coated in a fluid bed with a first layer composed of hydrogenated palm oil and a second layer composed of carnauba wax, for a total weight of 140 g (ratio between the two layers 6:4), to obtain a finished product containing 70% of vitamin C. The results of the release in vitro are given in chart 4.

Example 9

Vitamin C 816 g of vitamin C in crystals with an average diameter of approximately 0.5 mm is mixed with 92 g of carnauba wax, 92 g of microcrystalline wax and 6 g of magnesium stearate. The mixture is then made to pass through the extruder setting the temperatures of the different sectors with the following programme:

| Sector 1 | Sector 2 | Sector 3 | Sector 4 | Sector 5 | die |
|---|---|---|---|---|---|
| 60° C. | 75° C. | 50° C. | 45° C. | 40° C. | 65° C. |

The granules obtained in the form of cylindrical micropellets have a concentration of vitamin C equal to 80% and are coated in a fluid bed with a first layer composed of hydrogenated palm oil and a second layer composed of carnauba wax, for a total weight of 600 g (ratio between the two layers 6:4), to obtain a finished product containing 50% of vitamin C. The results of the release in vitro are given in chart 4.

CHART 4

| | | % release at 37° C. pH 5.8 | | | |
|---|---|---|---|---|---|
| Example | Titre % (vit. C) | After 1 hour | After 2 hours | After 5 hours | After 8 hours |
| 8 | 70.3 | 18.4 | 66.2 | 100 | / |
| 9 | 50.0 | 0.6 | 1.1 | 2.4 | 7.2 |

These examples tell us that it is extremely difficult to protect the highly water-soluble vitamin C too.

Example 10

Vitamin A Acetate 333.6 g of vitamin A acetate (2,100,000 U.I./g) is mixed with 150 g of carnauba wax, 314.4 g of microcrystalline wax, 2 g of BHT and 200 g of colloidal silica, the mixture is then made to pass through the extruder setting the temperatures of the different sectors with the following programme:

| Sector 1 | Sector 2 | Sector 3 | Sector 4 | Sector 5 | die |
|---|---|---|---|---|---|
| 80° C. | 102° C. | 50° C. | 45° C. | 40° C. | 65° C. |

The granules obtained have a concentration of vitamin A equal to 700,000 U.I./g and are coated in a fluid bed with a first layer composed of hydrogenated palm oil and a second layer composed of carnauba wax, for a total weight of 400 g (ratio between the two layers 3:7), to obtain a finished product containing vitamin A equal to 500,000 U.I./g. The results of the release in vitro are given in chart 5.

Example 11

Vitamin E Acetate 500 g of vitamin E acetate is mixed with 98 g of carnauba wax, 200 g of microcrystalline wax, 2 g of BHT and 200 g of colloidal silica, the mixture is then made to pass through the extruder setting the temperatures of the different sectors with the following programme:

| Sector 1 | Sector 2 | Sector 3 | Sector 4 | Sector 5 | die |
|---|---|---|---|---|---|
| 80° C. | 102° C. | 50° C. | 45° C. | 40° C. | 65° C. |

The granules obtained have a concentration of vitamin E acetate equal to 50% and are coated in a fluid bed with a first layer composed of hydrogenated palm oil and a second layer composed of carnauba wax, for a total weight of 250 g (ratio between the two layers 3:7), to obtain a finished product containing vitamin E acetate equal to 40%. The results of the release in vitro are given in chart 5.

CHART 5

| | | % release at 37° C. pH 5.8 | | | |
|---|---|---|---|---|---|
| Example | Titre | After 1 hour | After 2 hours | After 5 hours | After 8 hours |
| 10 | 502,000 UI/g | 0.0 | 0.2 | 0.6 | 0.8 |
| 11 | 50.1% | 0.0 | 0.1 | 0.2 | 0.4 |

Example 12

Vitamin $B_2$ 816 g of vitamin $B_2$ with an average diameter of 0.25 mm is mixed with 40 g of carnauba wax, 142 g of microcrystalline wax and 6 g of magnesium stearate, the mixture is then made to pass through the extruder setting the temperatures of the different sectors with the following programme:

| Sector 1 | Sector 2 | Sector 3 | Sector 4 | Sector 5 | die |
|---|---|---|---|---|---|
| 65° C. | 85° C. | 50° C. | 45° C. | 40° C. | 65° C. |

The granules obtained have a concentration of vitamin $B_2$ equal to 80% and are coated in a fluid bed with a first layer composed of hydrogenated palm oil and a second layer composed of carnauba wax, for a total weight of 600 g (ratio between the two layers 6:4), to obtain a finished product containing 50% of vitamin $B_2$. The results of the release in vitro are is given in chart 6.

Example 13

Vitamin PP 818 g of nicotinic acid (vitamin PP) with an average diameter of 0.600 mm is mixed with 86 g of carnauba wax, 90 g of microcrystalline wax and 6 g of magnesium stearate, the mixture is then made to pass through the extruder setting the temperatures of the different sectors with the following programme:

| Sector 1 | Sector 2 | Sector 3 | Sector 4 | Sector 5 | Die |
|---|---|---|---|---|---|
| 65° C. | 85° C. | 50° C. | 45° C. | 40° C. | 65° C. |

The granules obtained have a concentration of vitamin PP equal to 80% and are coated in a fluid bed with a first layer composed of hydrogenated soya oil and a second layer composed of carnauba wax, for a total weight of 600 g (ratio between the two layers 6:4), to obtain a finished product containing 50% of vitamin PP. The results of the release in vitro are given in chart 6.

CHART 6

| | | % release at 37° C. pH 5.8 | | | |
|---|---|---|---|---|---|
| Example | Titre % | After 1 hour | After 2 hours | After 5 hours | After 8 hours |
| 12 | 50.6 | 0.6 | 0.9 | 2.1 | 3.5 |
| 13 | 50.1 | 1.2 | 2.5 | 6.8 | 10.2 |

Example 14

Mixture of Acids 350 g of lactic acid 50%, 210 g of fumaric acid, 140 g of citric acid and 105 g of malic acid are mixed with 80 g of carnauba wax, 110 g of microcrystalline wax and 5 g of magnesium stearate, the mixture is then made to pass through the extruder setting the temperatures of the different sectors with the following programme:

| Sector 1 | Sector 2 | Sector 3 | Sector 4 | Sector 5 | die |
|---|---|---|---|---|---|
| 65° C. | 90° C. | 65° C. | 45° C. | 40° C. | 65° C. |

The granules obtained have a concentration of acids equal to 63% and are coated in a fluid bed with a first layer composed of hydrogenated soya oil and a second layer composed of carnauba wax, for a total weight of 260 g (ratio between the two layers 6:4), to obtain a finished product containing 50% of acids. The results of the release in vitro are given in chart 7.

CHART 7

| | | % release at 37° C. | % release at 37° C. pH 6.8 | |
|---|---|---|---|---|
| Example | Titre % | pH 2 After 2 hours | After 1 hour | After 3 hours |
| 14 | 50.6 | 0.9 | 50.9 | 100 |

In a preferred embodiment of this invention the composition in micro-pellets is administered to animals orally using the preparation of formula products (premixes or complementary foods). The composition is "diluted," by mechanical mixing, with a medium. The product obtained is ready to be added to the final feed.

Figure 2:
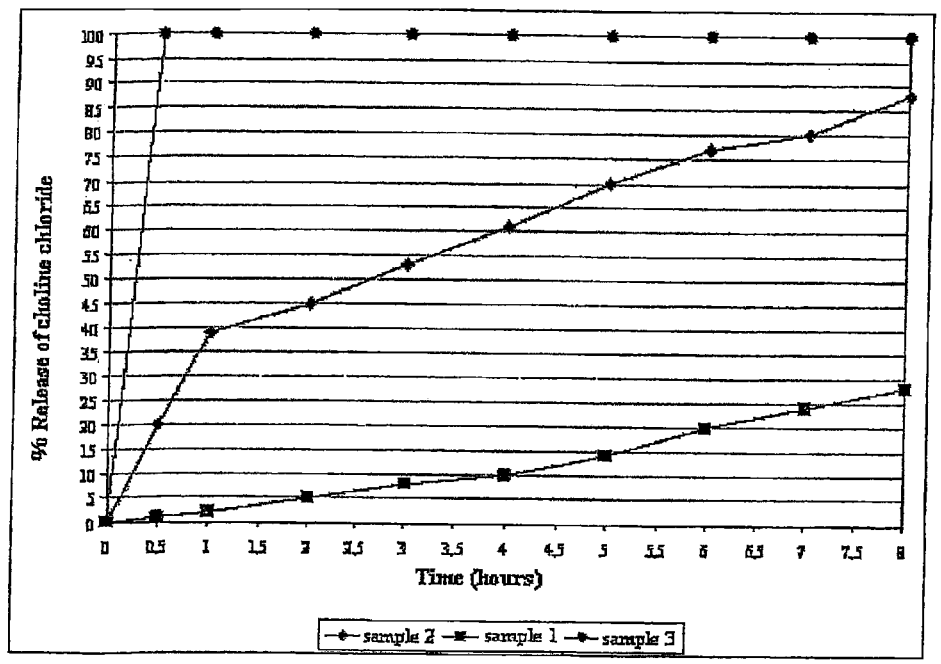
FIG. 2 shows in graphical view the percent release with time of an active principle from a granule according to the present invention, in comparison with the release of the same active principle from a granule obtained following the teaching of the art.

FIG. 2 is a graph showing a comparative test in vitro. The graph shows the release of the active ingredient (a.i.) choline chloride in relation to time in a phosphated buffer at pH 6 between:

sample 1: extruded granule with a double coating as described and claimed in this invention (50% in weight of choline chloride);

sample 2: non-extruded and non-coated granule prepared with the spray-congealing technique. In practice, the choline chloride (50% in weight) is mixed with fatty acids and waxes as the ones described above. The mixture is sprayed inside a tower at a temperature of 20-25° C. The granules cool and solidify in this tower. The choline remains incorporated in the granule.

sample 3: choline chloride as a raw material (98% in weight).

As shown in the graph, sample 1 has the most reduced release of a.i. compared to a similar granule that is neither extruded nor coated (sample 2).

What is claimed is:

1. A granule for animal feed for a ruminant with controlled release of a physiologically active substance, said granule comprising a core, a first layer surrounding the core, and a second layer surrounding the first layer, said core comprising a matrix along with one or more physiologically active substances selected from the group consisting of amino acids, vitamins, enzymes, proteins, carbohydrates, probiotic micro-organisms, prebiotic foods, mineral salts, choline, choline chloride, choline bi-tartrate, di-hydrogenated citrate of choline, bicarbonate of choline, choline sulphate, choline hydroxide, vitamin C acetate, and organic acids, said matrix comprising carnauba wax and/or microcrystalline wax, the layers together being effective to protect the physiologically active substance from ruminal activity while allowing effective release of the physiologically active substance into the post-rumen portion of the digestive tract of the ruminant, the first layer comprising a first hydrophobic substance selected from the group consisting of fats, fatty acids, hydrogenated oils, mono- and di-glycerides of fatty acids, esters of fatty acids, fatty alcohols, with chains from 12 to 22 atoms of carbon and a melting point of from 40 to 74° C., said first layer providing an effective water-repellent film that is stable under the conditions in the rumen for at least 8 hours, the second layer consisting of a second hydrophobic substance selected from the group consisting of microcrystalline waxes, paraffin waxes, vegetable waxes and synthetic waxes, the second layer having a melting point of from 80 to 100° C., said second layer being effective to protect the core and the first layer from degradation from pressure, impact and mechanical and thermal stress encountered during mixing and pelletization of said granules into an animal feed pellet.

2. The granule according to claim 1 wherein the physiologically active substance is selected from the group consisting of: methionine, choline, choline chloride, lysine, vitamin C, vitamin C acetate, vitamin E, vitamin $B_2$, vitamin PP and a mixture of acids comprising lactic acid, fumaric, citric and malic acid.

3. The granule according to claim 1, wherein the matrix contains carnauba wax and microcrystalline wax in a weight ratio of from 1:3 to 3:1.

4. The granule according to claim 1 wherein the matrix contains only microcrystalline wax.

5. The granule according to claim 1 wherein the first hydrophobic substance has a melting point of from 60 to 64° C.

6. The granule according to claim 1 wherein the first hydrophobic substance is selected from the group consisting of: lauric acid, stearic acid, palmitic acid, stearine, hydrogenated soya oil, hydrogenated cotton oil, hydrogenated palm oil, hydrogenated linseed oil, sodium glyceril mono-, di-, tri-stearate, calcium stearate, magnesium stearate, stearyl alcohol, and cetyl stearyl alcohol.

7. The granule according to claim 1 wherein the first hydrophobic substance is hydrogenated palm oil and/or hydrogenated soya oil.

8. The granule according to claim 1 wherein the second hydrophobic substance is carnauba wax and/or microcrystalline wax.

9. The granule according to claim 1 wherein the matrix moreover includes hydrophobic silicates selected from the group consisting of: colloidal silica, amorphous synthetic silica, precipitated silica, sodium aluminium silicates, calcium silicate, talc, kaolin, synthetic hydrophobic zeolites, magnesium stearate and BHT.

10. The granule according to claim 1 wherein the granule has a cylindrical shape with a diameter of from 0.5 to 5 mm; and a length of from 0.5 to 5 mm.

11. A procedure for the preparation of a granule for animal feed according to claim 1, the procedure comprising the following steps: (1) extrusion of a composition comprising (a) one or more physiologically active substances selected from the group consisting of: amino acids, vitamins, enzymes, proteins, carbohydrates, probiotic micro-organisms, prebiotic foods, mineral salts, choline, choline chloride, choline bi-tartrate, di-hydrogenated citrate of choline, bicarbonate of choline, choline sulphate, choline hydroxide, vitamin C acetate, and organic acids and (b) a matrix comprising a carnauba wax and/or a microcrystalline wax, to yield a core; (2) formation of a first layer around the core, the first layer comprising a first hydrophobic substance selected from the group consisting of: fats, fatty acids, hydrogenated oils, mono- and di-glycerides of fatty acids, esters of fatty acids, fatty alcohols, with chains from 12 to 22 atoms of carbon and a melting point of from 40 to 74° C.; and (3) formation of a second layer around the first layer, the second layer consisting of a second hydrophobic substance selected from the group consisting of: microcrystalline waxes, paraffin waxes, vegetable waxes and synthetic waxes, the second layer having a melting point of from 80 to 100° C., the procedure yielding the granule for animal feed according to claim 1.

12. The procedure according to claim 11 wherein the first and the second layers are made with a hot melt coating technique.

13. The procedure according to claim 11 wherein the physiologically active substance is selected from the group consisting of: methionine, choline, choline chloride, lysine, vitamin C, vitamin C acetate, vitamin E, vitamin $B_2$, vitamin PP and a mixture of acids comprising lactic acid, fumaric, citric and malic acid.

14. The procedure according to claim 11 wherein the matrix contains carnauba wax and microcrystalline wax in a weight ratio of from 1:3 to 3:1.

15. The procedure according to claim 11 wherein the first hydrophobic substance has a melting point of from 60 to 64° C.

16. The procedure according to claim 11 wherein the first hydrophobic substance is selected from the group consisting of: lauric acid, stearic acid, palmitic acid, stearine, hydrogenated soya oil, hydrogenated cotton oil, hydrogenated palm oil, hydrogenated linseed oil, sodium glyceril mono-, di-, tri-stearate, calcium stearate, magnesium stearate, stearyl alcohol, and cetyl stearyl alcohol.

17. A premix for animal feeding containing the granule according to claim 1.

18. The premix according to claim 17, said premix being in a feed for animal feeding.

19. The granule according to claim 1, wherein the matrix contains carnauba wax and microcrystalline wax in a weight ratio of 1:1.

20. The granule according to claim 1, wherein the granule has a substantially cylindrical shape with a diameter of from 0.8 to 1.2 mm and a length of from 0.8 to 2.0 mm.

21. The granule according to claim 1, wherein the second hydrophobic substance is selected from the group consisting of microcrystalline waxes.

22. The granule according to claim 1, wherein the second hydrophobic substance is selected from the group consisting of vegetable waxes.

23. The granule according to claim 1, wherein the second hydrophobic substance is carnauba wax.

* * * * *